United States Patent [19]

Seid et al.

[11] 4,428,373
[45] Jan. 31, 1984

[54] DISPOSABLE DENTAL TRAY

[75] Inventors: Paul Seid, New City; Herbert Wolf, Pomona, both of N.Y.

[73] Assignee: Sultan Dental Products Limited, Englewood, N.J.

[21] Appl. No.: 345,539

[22] Filed: Feb. 3, 1982

[51] Int. Cl.³ .............................................. A61M 35/00
[52] U.S. Cl. ........................................ 604/77; 433/80; 604/57
[58] Field of Search .............. 433/80, 42, 6; 128/136, 128/260

[56] References Cited

U.S. PATENT DOCUMENTS 4,173,219  11/1979  Lentine ............................... 128/136

Primary Examiner—Robert Peshock
Attorney, Agent, or Firm—Steinberg & Raskin

[57] ABSTRACT

A disposable dental tray for medications such as fluoride gel, includes a unitary member formed of a flexible foam material defining a pair of hinged U-shaped tray portions configured to fit over the upper and lower teeth of the mouth and wherein each tray portion is defined by a base wall, a pair of end walls and inner and outer side walls. Both of the tray portions are provided with respective tray portion positioning tabs extending from their respective outer side walls. The positioning tabs include respective tab sections which are preformed so as to be situated such that when the tray portions are folded, the respective tab sections will automatically abut and be squeezable against each other without the consequent application of any forces to the outer side walls of the tray portion thereby preventing any possibility of distorting the tray portions during use.

5 Claims, 3 Drawing Figures

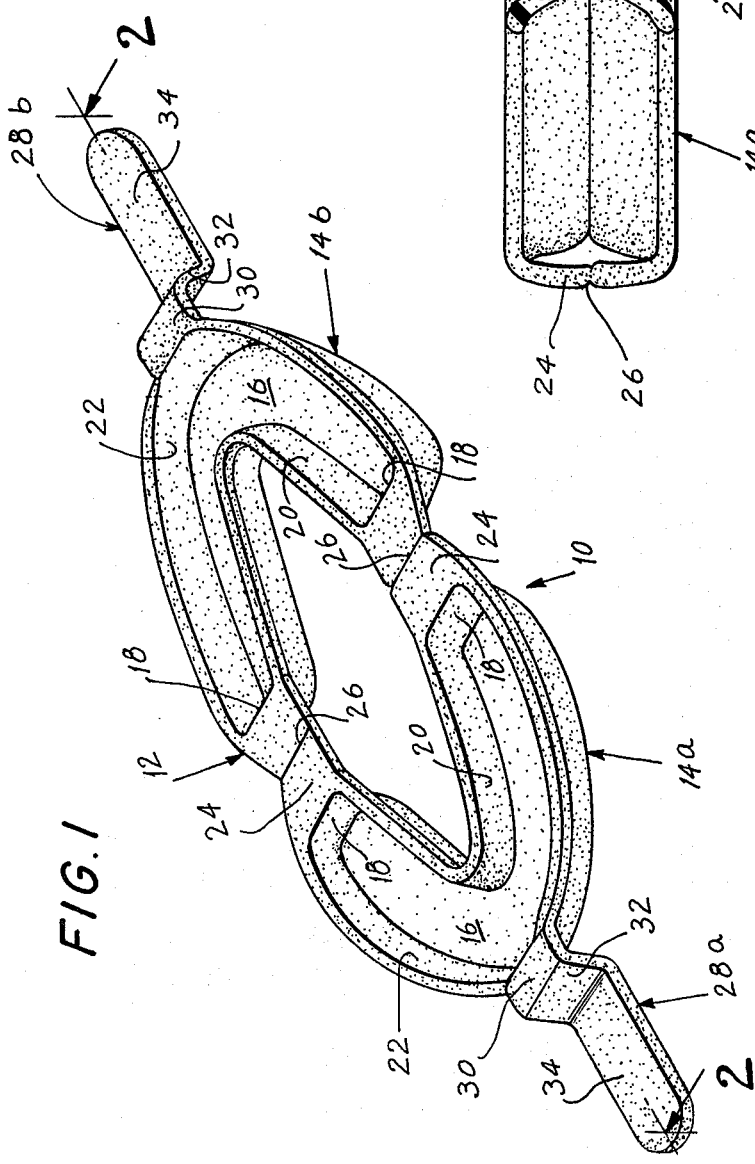
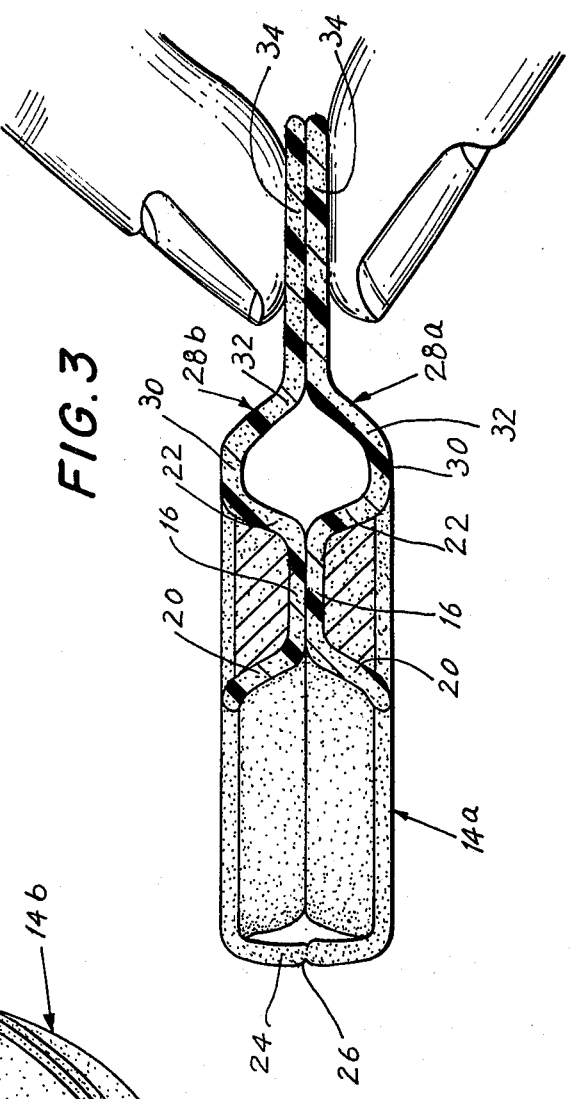
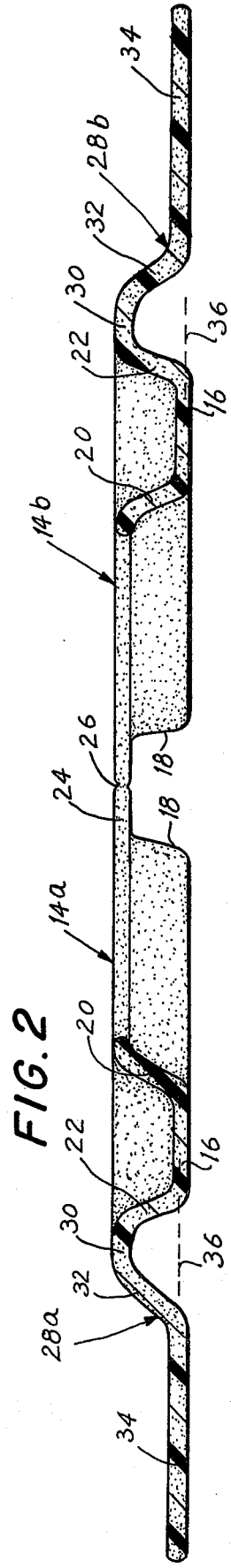

4,428,373

DISPOSABLE DENTAL TRAY

BACKGROUND OF THE INVENTION

This invention relates generally to the application of dental medication to the teeth and, more particularly, to a disposable dental tray for use in the topical application of dental medications, such as fluoride gel or the like, to the teeth.

Periodic topical application of fluoride to the teeth is a common dental procedure. Such treatment is generally performed in the dentist's office using a tray having a tray portion formed therein having a configuration such that it will fit over either the upper or lower teeth of the mouth. The tray portion is filled with the desired dosage of fluoride gel whereupon it is fit over the teeth to be treated.

Although it has been conventional in the past to utilize reusable trays having disposable inserts formed of foam or sponge-like material in connection with such fluoride treatment, trays which are completely disposable have been developed. Such trays, typical examples of which are illustrated in U.S. Pat. Nos. 3,955,281 and 3,527,219, are generally also formed of a foam material. In both cases, after the tray is placed into the mouth, the patient bites down whereupon the fluoride is forced around the teeth.

Disposable dental trays formed of foam or the like and having a pair of hinged tray portions specifically designed to conform to the geometry of both the upper and lower teeth, respectively, are also known, an example being illustrated in U.S. Pat. No. 4,173,219. The tray portions are hinged to each other by a pair of integral hinge portions with respect to which the tray can be folded until the tray portions which have been filled with fluoride obtain their in-use position. Such trays are advantageous in that the upper and lower teeth can be treated simultaneously thereby reducing the time of treatment.

Experience has shown that difficulties often arise in connection with the handling of such hinged, double trays during use. More particularly, it has been conventional practice to provide each tray portion with an integral handle extending outwardly therefrom by which the tray can be grasped. When the tray portions are folded to the in-use position, the handles are bent and pinched together between the thumb and forefinger of the user. However, when the handles are bent and pinched together in this manner, forces are unavoidably applied by the handles to the tray portions which tend to distort the tray portions. This is extremely disadvantageous in that the medicament contained in the tray portions may spill therefrom over a distorted wall portion thereof. In an attempt to overcome this problem in trays which include an outer vacuum formed shell of polyethylene in addition to the inner layer of foam material, score lines have been formed in the outer shell of the handles to facilitate their bending. In this connection, reference is made to the above-mentioned U.S. Pat. No. 4,173,219. However, even where such score lines are provided, deleterious distorting forces are still unavoidably exerted on the tray portions when the handles are squeezed together.

In order to minimize the forces exerted on the tray portions, a user will tend to grasp the handles at a position as close to the tray portions as possible. However, this results in the fingers touching the region of the mouth which, of course, is not entirely hygienic.

SUMMARY OF THE INVENTION

Accordingly, one object of the present invention is to provide a new and improved disposable hinged double dental tray for use in connection with the topical application of medication, e.g., for a gel, to the teeth whereby the drawbacks noted above are eliminated.

Briefly, in accordance with the present invention, these and other objects are attained by providing a disposable dental tray for medication such as fluoride gel including a unitary member formed of a flexible foam material defining a pair of hinged U-shaped tray portions configured to fit over the upper and lower teeth, and each tray portion being defined by a base wall, a pair of end walls and inner and outer side walls.

Both of the tray portions are provided with respective tray portion positioning tabs extending from their respective outer side walls. The positioning tabs include respective tab sections which are pre-formed so as to be situated such that when the tray portions are folded, the respective tab sections will automatically abut and be squeezable against each other without a consequent application of any substantial forces to the outer side walls of the tray portions thereby preventing any possibility of distorting the tray portions.

In the illustrated embodiment of the invention, each positioning tab is pre-formed so as to extend from the free upper edge of the outer side wall of a respective tray portion, extend generally downwardly toward the base wall of the tray portion, and terminate in a tab section which extends outwardly generally in the same plane as the tray portion base wall. In use, the tray portions are filled with medicament and then folded until the pre-formed tab sections automatically abut. In this configuration, the tray portions will be in the in-use position, i.e., with the base wall of the tray portions being substantially contiguous to each other. The tab sections can be squeezed together with any desired degree of pressure to ensure reliable handling and without any consequent forces being exerted on the tray portions which would distort the same and possibly result in spillage of the medicament contained therein. The additional advantage is obtained that the user can grasp the positioning tab at a location somewhat remote from the tray itself so as to ensure a completely hygienic application of the medicament.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is a perspective view of the disposable dental tray according to the present invention;

FIG. 2 is a section view taken along line 2—2 of FIG. 1; and

FIG. 3 is a side elevation view of the tray in its in-use position and illustrating the application of a squeezing pressure to the tray portion positioning tabs.

DETAILED DESCRIPTION OF THE PREFERRED EMBODIMENTS

Referring now to the drawings wherein like reference characters designate identical or corresponding parts throughout the several views, a disposable dental tray 10 according to the present invention for the topical application of a medicament, such as a fluoride gel, to the teeth is illustrated.

The tray 10 includes a unitary member 12 formed from a flexible foam material, preferably a closed cell polyethylene foam material, and defines a pair of troughs or tray portions 14a and 14b, each configured to fit over either one of the upper or lower teeth of the mouth. Thus, each tray portion 14 is formed by a base wall 16, a pair of end walls 18 and inner and outer side walls 20 and 22 respectively. Each of the pair of end walls 18 associated with a particular one of the tray portions is in spaced opposed relationship to a respective one of the pair of end walls 18 of the other tray portion as best seen in FIG. 2. A pair of hinge portions 24 integrally extend between respective pairs of opposed end walls 18 to interconnect the tray portions 14a and 14b. A fold line 26 may be provided in each hinge portion 24 to facilitate folding of the tray into its in-use position illustrated in FIG. 3

According to the present invention, both of the tray portions 14a and 14b are provided with respective tray portion positioning tabs 28a and 28b integrally extending outwardly from the respective outer side walls 22 thereof. The positioning tabs 28a and 28b illustrated in the preferred embodiment are pre-formed during manufacture of the tray, such as by molding or the like, so as to each include a first portion 30 which extends outwardly from the free upper edge of the respective outer side wall 22, a second portion 32 which extends generally toward the base wall 16 of the respective tray portion and a terminal tab section 34 which extends outwardly substantially in the region of the plane, designated 36 in FIG. 2, of the base wall 16 of the respective tray portion. In this connection, the tab sections 34 need not necessarily lie in precisely the plane 36 of base walls 16, but may extend slightly above or below the plane, and it is understood that such positioning is encompassed by the term "in the region of the plane".

In use, the tray portions 14a and 14b are filled with fluoride gel or other medicament while in the configuration illustrated in FIGS. 1 and 2. The tray portions 14a and 14b are then folded on hinge portions 24 toward the in-use position illustrated in FIG. 3. According to the construction of the present invention, the pre-formed tab sections 34 will automatically abut when the tray 10 is in the in-use position, i.e., when the base wall 16 of the tray portions 14a and 14b are substantially contiguous. Depending upon the exact location of tab sections 34, i.e., whether they are in the planes 36 of respective base walls 16 or are slightly above or below the same, the base walls 16 of the tray portions 14a and 14b may be slightly spaced or may touch each other. However, it is understood that in the case where the base walls do touch at one or more points, i.e., where tab sections 34 lie somewhat above the planes of respective base walls 16 so that upon folding the tray portions the tab sections 34 are slightly spaced from each other, only an insignificant force will be exerted on the outer side walls of the tray portions by the positioning tabs 28 which is insufficient to cause any substantial deformation thereof.

Thus, the tab sections 34 can be squeezed together with any desired pressure to ensure reliable handling of the tray with little or no forces being exerted on the tray portions which would distort the same and possibly result in spillage of the medicament contained therein.

It is also apparent from FIG. 3 that the user can grasp the positioning tabs at a location somewhat remote from the tray portions themselves in order to ensure a completely hygienic application, i.e., without any possibility of the fingers touching the region of the mouth.

The tray portion positioning tabs may have a configuration other than that shown in the drawings. For example, the second tab portion 32 may extend toward the base wall 16 of a respective tray portion so as to form a substantial right angle with the first tab portion 30 and tab section 34. Alternatively, the positioning tabs may extend outwardly from outer side walls 22 directly from a bottom region thereof which substantially lies in the region of the plane of the base walls. In this embodiment, each tab may comprise only a single planar tab section. Thus, it is understood that the present invention essentially constitutes the provision of positioning tabs which are pre-formed so as to be situated such that when the tray portions are folded, the respective tab sections will substantially automatically abut or at most be slightly spaced each other; and be squeezable against each other without the consequent application of any forces which would distort the outer side walls of the tray portions.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. In a disposable dental tray for topical application of dental medications to the teeth including a unitary member formed of a flexible foam material defining a pair of U-shaped tray portions connected to each other by hinge means and configured to fit over the upper and lower teeth of the mouth respectively when the tray portions are folded around the hinge means, and a tab extending outwardly from each of said tray portions, the improvement comprising:

said tabs include respective tab sections which are pre-formed so as to be situated such that when the tray portions are folded, the respective tab sections will contiguously mutually confront each other in the absence of any external forces being applied thereto and be squeezable against each other without the consequent application of any substantial forces on said tray portions which would distort the same, said tabs thereby constituting tray portion positioning tabs.

2. The combination of claim 1 wherein each tray portion is defined by a base wall, a pair of end walls and inner and outer side walls and wherein said pre-formed tray portion positioning tabs extend integrally and outwardly from said outer side walls of the respective tray portions.

3. The combination of claim 2 wherein each of said tab sections extends substantially in the region of the plane of the base wall of a respective tray portion.

4. The combination of claim 2 wherein each tray portion positioning tab includes a first portion extending outwardly from an upper free edge of a respective outer side wall, a second portion extending toward a respective base wall and said tab section extending in the region of the plane of said respective base wall.

5. In a disposable dental tray for topical application of dental medications to the teeth including a unitary member formed of a flexible foam material defining a pair of hinged U-shaped tray portions configured to fit over the upper and lower teeth of the mouth respectively, each tray portion including a base wall, a pair of end walls and inner and outer side walls, and a tab extending outwardly from an upper edge of an outer side wall of each of the tray portions, the improvement comprising: said tabs each including a pre-formed section which extends from the region of the upper edge of the outer side wall towards the base wall of the respective tray portion in the absence of any external forces being applied thereto.

* * * * *